United States Patent [19]
Beissner et al.

[11] Patent Number: 5,270,647
[45] Date of Patent: Dec. 14, 1993

[54] PIPE ELECTROMAGNETIC FIELD SIMULATION APPARATUS USING BORN'S APPROXIMATION RULE

[75] Inventors: Robert Beissner, San Antonio, Tex.; Takashi Kikuta, Ikoma, Japan

[73] Assignee: Osaka Gas Company, Ltd., Osaka, Japan

[21] Appl. No.: 818,148

[22] Filed: Jan. 8, 1992

[51] Int. Cl.$^5$ .................. G01N 27/82; G01N 27/90; G01R 33/12
[52] U.S. Cl. .................................. 324/240; 324/220; 324/228; 364/578
[58] Field of Search ............... 324/202, 226, 227, 232, 324/233, 238, 239-243; 364/578

[56] References Cited
U.S. PATENT DOCUMENTS 3,693,075  9/1972  Forster .............................. 324/241
4,763,274  8/1988  Junker et al. ..................... 324/220 X
4,855,677  8/1989  Clark, Jr. et al. ............... 324/220 X

*Primary Examiner*—Gerard R. Strecker
*Attorney, Agent, or Firm*—Beveridge, DeGrandi, Weilacher & Young

[57] ABSTRACT

A pipe electromagnetic field simulation apparatus used to simulate a current produced by flaw in a pipe when the flaw is subjected to the electromagnetic field of a transmitting coil. The apparatus includes a system for determining an electromagnetic field distribution of a represented pipe without a flaw, a system for determining an equivalent current source of a represented flaw in the represented pipe, and a system for determining the electromagnetic field distribution of a represented pipe with a flaw. The apparatus may also include a system for determining a signal received by a detector which indicates a flaw.

4 Claims, 5 Drawing Sheets

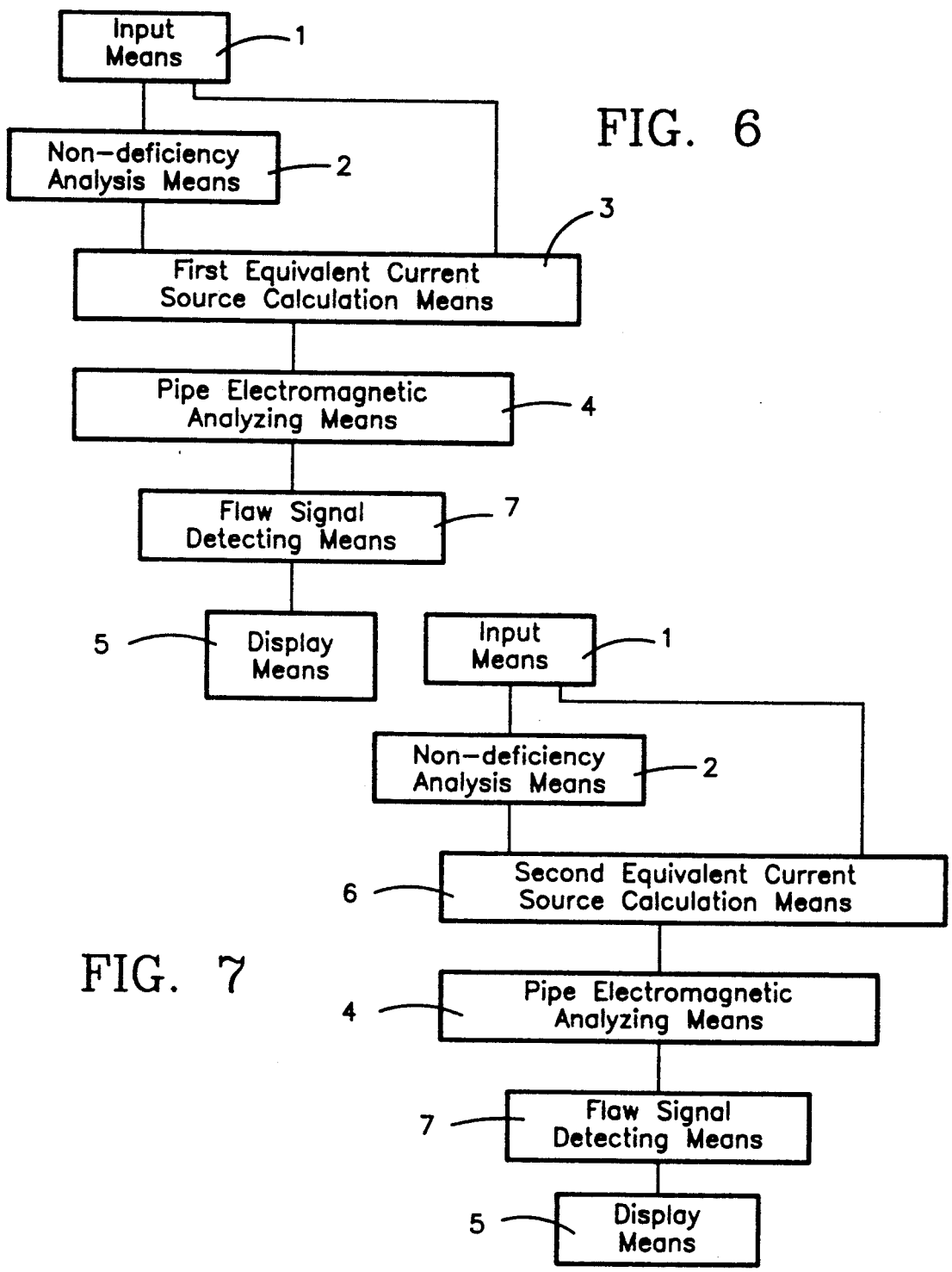

PIPE ELECTROMAGNETIC FIELD SIMULATION APPARATUS USING BORN'S APPROXIMATION RULE

BACKGROUND OF THE INVENTION

1. Field of the Invention

The present invention relates to a pipe electromagnetic field simulation apparatus which is used to detect a flaw existing in a pipe.

2. Description of the Related Art

Where a flaw existing in a pipe is to be detected, there has been known a method of detecting the flaw in the pipe by moving a transmitting coil for generating a magnetic field while moving a receiving coil for receiving the magnetic field in a manner corresponding with the transmitting coil.

The transmitting coil generates a magnetic field with a predetermined magnitude, thereby causing an eddy current to flow in the pipe. The flow of the eddy current causes an indirect magnetic field to be generated near the pipe. The receiving coil detects the indirect magnetic field. If the pipe has a flaw, then the magnitude and phase of the magnetic field received will change as compared with that without flaw. By picking up the change in magnitude and phase of the magnetic field, the size and phase of the flaw of the pipe are detected.

However, the above-mentioned detecting method has had a problem in that a pipe to be detected has various sizes, whereby a transmitting coil and a receiving coil which are just fit for the size of the pipe must be produced each time the detection is performed, and many experiments be conducted to obtain the relationship with a flaw.

A method of detecting the relationship of a transmitting coil and a receiving coil with a flaw by a simulation technique may be assumed. However, the method and the like which are simple applications of conventional analysis techniques may not be performed successfully because of the following reason.

A pipe is made of an electrically-conductive material. A depth $\delta$ to which electromagnetic field penetrates an electrically-conductive material is generally represented by the following equation.

$$\delta = \sqrt{(2/(\omega\sigma\mu))} = 1/\sqrt{(3.95 \times 10^{-6} \times f\sigma\mu s)} \ [m]$$

where $\delta$ = a depth at which magnitude of electromagnetic field incident on electrically-conductive material attenuates to $1/e$ ($e = 2.718\ldots$) of magnitude at surface of electrically-conductive material $\omega = 2\pi f$
f = frequency
$\sigma$ = electric conductivity(S/m)
$\mu s$ = specific permeability For a steel pipe with $\sigma = 3.30 \times 10^6$ and $\mu s = 400$, its penetration depth $\delta$ becomes as very small as $1.95 \times 10^{-3}$(m). This mean that steel pipes have a strong magnetic property, whereby a large shield effect is produced and thus the generation of eddy current is biased inward. On the other hand, a corroded flaw occurring on gas pipes is likely to appear on their external surface. Accordingly, the eddy current due to the corroded flaw varies very slightly.

Because of such conditions, in order to analyze a steel pipe by utilizing, for example, the boundary element method, it is necessary to divide the surface of the pipe by a triangle having a side of about 2 mm. This means that in order to analyze, for example, a pipe having a diameter 5 cm and a length 30 cm, it is necessary to divide its lateral length by 75 ($50 \times 3.14 \div 2$) and its longitudinal length by 150 ($300 \div 2$). Accordingly, it is necessary to divide the surface into about 10,000 elements with square mesh, or into 20,000 elements with triangle mesh, that is, in total about 40,000 elements for its external and internal surfaces. However, where the boundary element analysis is performed by using a supercomputer, its upper limit is about 5,000 elements, so that the analysis is practically impossible.

SUMMARY OF THE INVENTION

The present invention has been devised to solve the problem of such prior art simulation techniques, and the object thereof is to provide a pipe electromagnetic field simulation apparatus capable of simply performing simulation.

That is, a pipe electromagnetic field simulation apparatus of the present invention comprises:
- input means for inputting various data relating at least to a pipe to be detected for flaw, to a transmitting coil, to the exciting frequency of the transmitting coil, and to a flaw,
- non-flaw analysis means for analyzing the electromagnetic field distribution of the pipe assuming that the pipe has no flaw based on the various data from the input means,
- first equivalent current source calculation means for determining a current source equivalent to the flaw by utilizing the various data inputted from the input means and the results analyzed by the non-flaw analysis means, and by performing repeatedly a calculation according to Born's approximation rule, and
- pipe electromagnetic field analysis means for analyzing the electromagnetic field of the pipe having the flaw by utilizing the results calculated by the first equivalent current source calculation means.

A pipe electromagnetic field simulation apparatus of the present invention, which moves a transmitting coil in a pipe to be detected for flaw and detects a flaw of the pipe, the apparatus comprises;
- input means for inputting various data relating at least to the pipe, to the transmitting coil, to the exciting frequency of the transmitting coil, and to the flaw,
- non-flaw analysis means for analyzing the electromagnetic field distribution of the pipe by assuming that the pipe has no flaw based on the various data from the input means,
- second equivalent current source calculation means;
  for determining a current source equivalent to the flaw by utilizing the various data inputted from the input mean and the results analyzed by the non-flaw analysis means, and by performing repeatedly a calculation according to Born's approximation rule in case of a calculation where the transmitting coil is located in a first position, and
  for determining an equivalent current source by making the equivalent current source proportional to the magnitude of the electromagnetic field, in the flaw position for non-flaw, obtained by the non-flaw analysis means and thus correcting the equivalent current source previously determined in case of a calculation where the transmitting coil is located in a second and subsequent positions, and pipe electromagnetic field analysis means for analyzing the electromagnetic field of the pipe having the flaw by utilizing the results calculated by the second equivalent current source calculation means.

A pipe electromagnetic field simulation apparatus of the present invention comprises;

input means for inputting various data relating at least to a pipe to be detected for a flaw, to a transmitting coil, to the exciting frequency of the transmitting coil, to a flaw, to a receiving coil, and to a distance between the transmitting coil and the receiving coil, non-flaw analysis means for analyzing the electromagnetic field distribution of the pipe assuming that the pipe has no flaw based on the various data from the input means, first equivalent current source calculation means for determining a current source equivalent to the flaw by utilizing the various data inputted from the input means and the results analyzed by the non-flaw analysis means, and by performing repeatedly a calculation according to Born's approximation rule, pipe electromagnetic field analysis means for analyzing the electromagnetic field of the pipe having the flaw by utilizing the results calculated by the first equivalent current source calculation means, and flaw signal detecting means for calculating a flaw signal produced in the receiving coil by utilizing the results calculated by the pipe electromagnetic field analysis means.

A pipe electromagnetic field simulation apparatus of the present invention, which moves a transmitting coil in a pipe to be detected for a flaw and detects a flaw of the pipe, the apparatus comprises;

input means for inputting various data relating at least to the pipe, to the transmitting coil, to the exciting frequency of the transmitting coil, to the flaw, to a receiving coil, and to a distance between the transmitting coil and the receiving coil, non-flaw analysis means for analyzing the electromagnetic field distribution of the pipe by assuming that the pipe has no flaw based on the various data from the input means, second equivalent current source calculation means;

for determining a current source equivalent to the flaw by utilizing the various data inputted from the input means and the results analyzed by the non-flaw analysis means, and by performing repeatedly a calculation according to Born's approximation rule in case of a calculation where the transmitting coil is located in a first position, and for determining an equivalent current source by making the equivalent current source proportional to the magnitude of the electromagnetic field, in the flaw position for non-flaw, obtained by the non-flaw analysis means and thus correcting the equivalent current source previously determined in case of a calculation where the transmitting coil is located in a second and subsequent positions, pipe electromagnetic field analysis means for analyzing the electromagnetic field of the pipe having the flaw by utilizing the results calculated by the second equivalent current source calculation means, and flaw signal detecting means for calculating flaw signal produced in the receiving coil by utilizing the results calculated by the pipe electromagnetic field analysis means.

BRIEF DESCRIPTION OF THE DRAWINGS

FIG. 6 is a block diagram showing a pipe electromagnetic field simulation apparatus according to a third embodiment of the present invention.

FIG. 7 is a block diagram showing a pipe electromagnetic field simulation apparatus according to a fourth embodiment of the present invention.

DESCRIPTION OF THE PREFERRED EMBODIMENTS

With reference to drawings, one embodiment of the present invention will be explained hereinafter.

Figure 1:
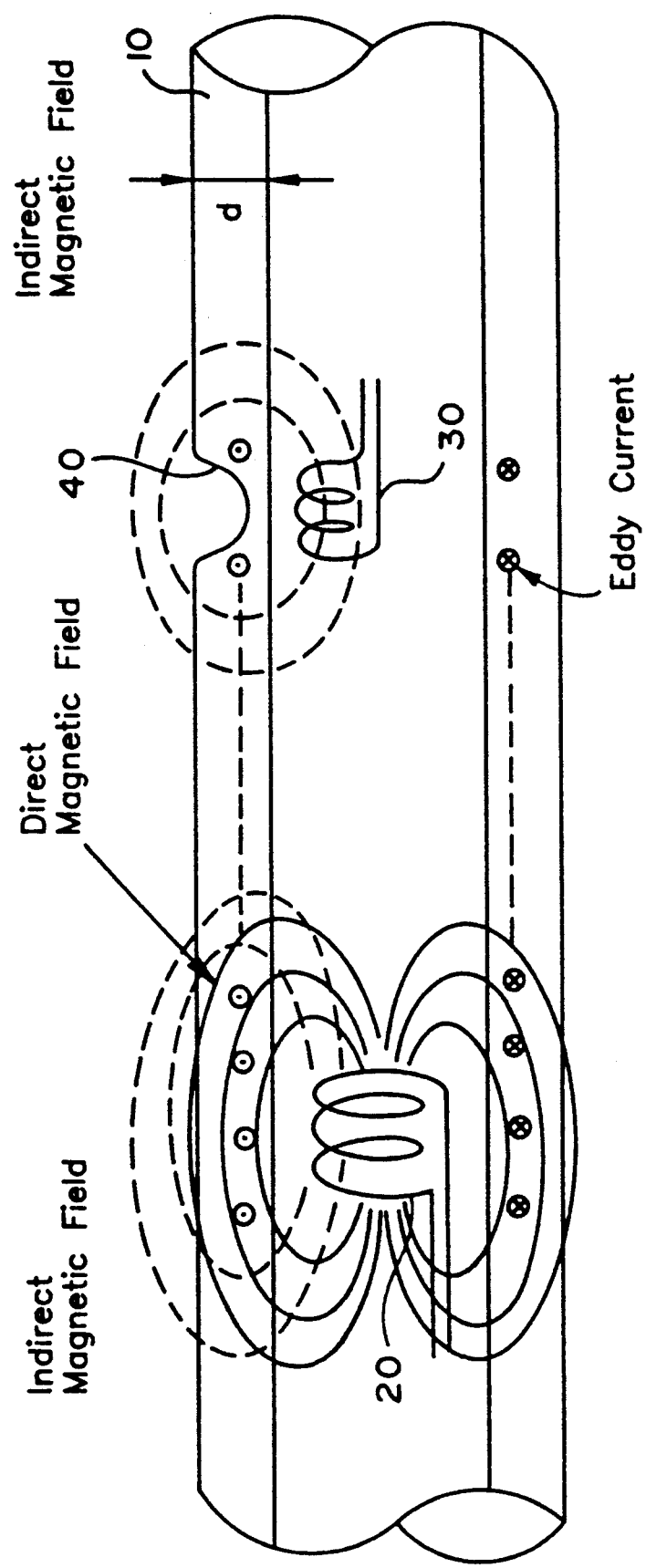
FIG. 1 is a schematic sectional view showing a pipe, a transmitting coil and the like which are to be provided by a pipe electromagnetic field simulation apparatus according to the present invention.

FIG. 1 is a conceptual view showing a status in which a pipe is detected for flaw by the use of a transmitting coil and a receiving coil, the status being an object of a pipe electromagnetic field simulation apparatus according to the present invention. In FIG. 1, a transmitting coil 20 is disposed in a steel pipe 10 having a wall thickness d so as to move axially in the pipe 10. A receiving coil 30 is also disposed apart by a specified distance from the transmitting coil 20. A corroded concavity (hereinafter called corrosion concavity) 40 also exists on the external surface of the pipe 10. In such condition, the transmitting coil 20 together with the receiving coil 30 are allowed to move in the pipe 10. Then, a direct magnetic field is generated from the transmitting coil 20, whereby an eddy current is generated in the pipe 10 to cause an indirect magnetic field to be generated. The receiving coil 30 picks up the indirect magnetic field to output the field as a voltage. Accordingly, the generated voltage of the receiving coil 30 at a place where the corrosion concavity 40 exists becomes different from that at a place where no corrosion concavity 40 exists. The difference is picked up to detect the corrosion concavity 40. This apparatus is operated by simulating such flaw detecting method.

Figure 2:
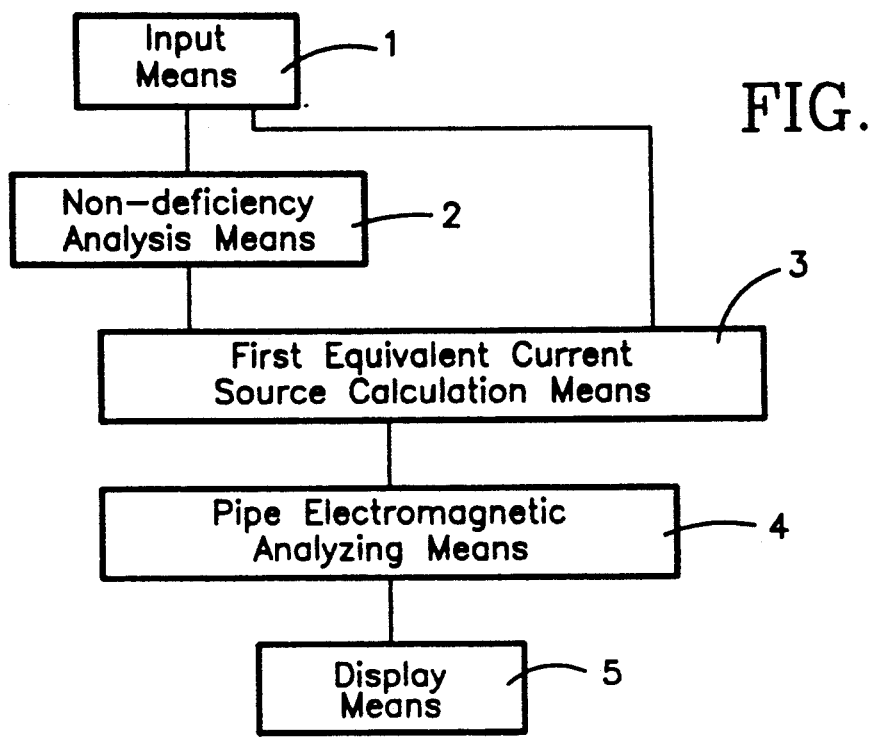
FIG. 2 is a block diagram showing a pipe electromagnetic field simulation apparatus according to a first embodiment of the present invention.

FIG. 2 is a block diagram showing a pipe electromagnetic field simulation apparatus according to a first embodiment of the present invention. In FIG. 2, input means 1 are a keyboard, a mouse and the like for inputting the following various data.

That is, input data such as the dimensional data relating to the diameter, wall thickness and length of a pipe to be detected, the specific permeability of the pipe, the dielectric constant of the pipe, the dimension of a transmitting coil (outside diameter, length), the number of turns of the transmitting coil, the magnitude of an exciting current, the frequency of the exciting current, the gap between the transmitting coil and a receiving coil, the dimension of the receiving coil (outside diameter, length), the number of turns of the receiving coil, the gap between the receiving coil and the internal surface of the pipe (lift off), the orientation of the receiving coil (in the axial direction, the radial direction or peripheral direction), the shape, dimension and position of a flaw (corrosion concavity), as well as the following calculating conditions are input into the input means.

The calculating conditions are as follows: the scan length of the receiving coil (from the start point to the end point in the pipe axial direction), the number of the calculating points in the axial direction, the number of turns of the receiving coil in the pipe peripheral direction, the peripheral gap of the receiving coil, and the like.

Non-deficiency analysis means 2 analyze an electromagnetic field distribution by utilizing various data from the input means 1 and by assuming that the pipe has no flaw, and will be explained in detail later.

First equivalent current calculation means 3 determine a current source equivalent to the flaw by utilizing various data input from the input means 1 and the results analyzed by said non-deficiency analysis means 2, and by performing repeatedly a calculation according to the Born's approximation rule, and will be explained in detail later.

Pipe electromagnetic field analysis means 4 analyzes the electromagnetic field of the pipe having the flaw by utilizing the results calculated by the first equivalent current source calculation means 3, and will be explained in detail later.

Display means 5 are a display, a printer and the like for displaying the results analyzed by the pipe electromagnetic field analysis means 4.

Figure 3:
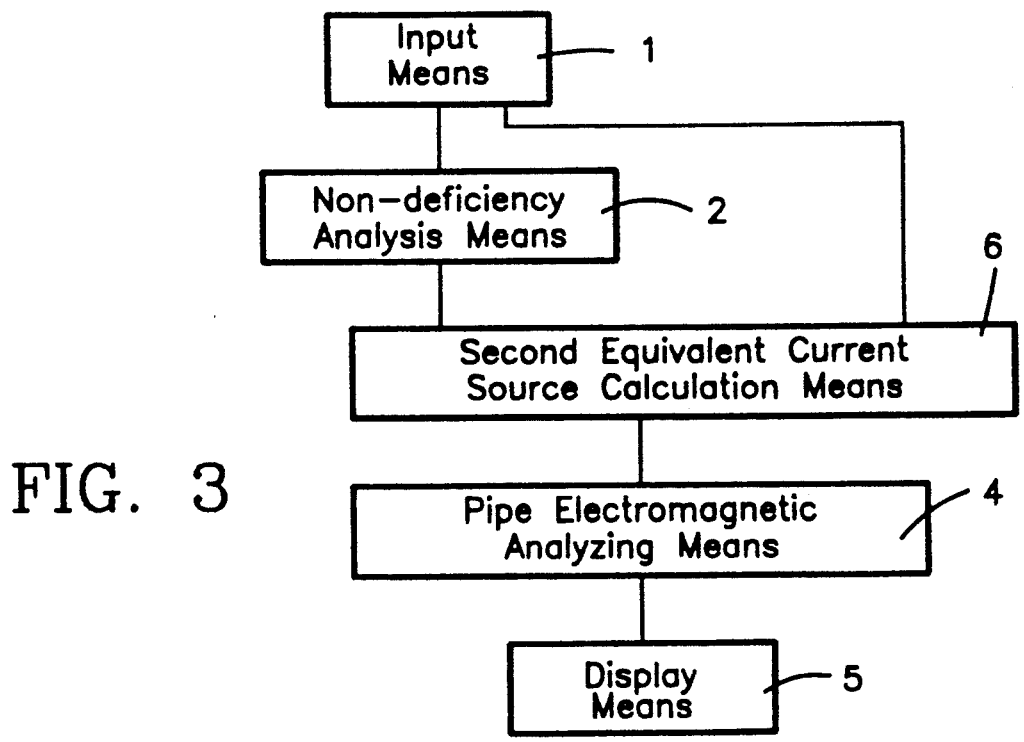
FIG. 3 is a block diagram showing a pipe electromagnetic field simulation apparatus according to a second embodiment of the present invention.

FIG. 3 is a block diagram showing a pipe electromagnetic field simulation apparatus according to a second embodiment of the present invention. The second embodiment is different from the first embodiment in that the second embodiment employs second equivalent current calculation means 6 instead of the first equivalent current calculation means 3 to allow a simple calculation method where a simulation is performed while the transmitting coil is allowed to move in the pipe.

The operation of the embodiments according to both the first embodiment and the second embodiments will be simultaneously explained hereinafter.

Figure 4:
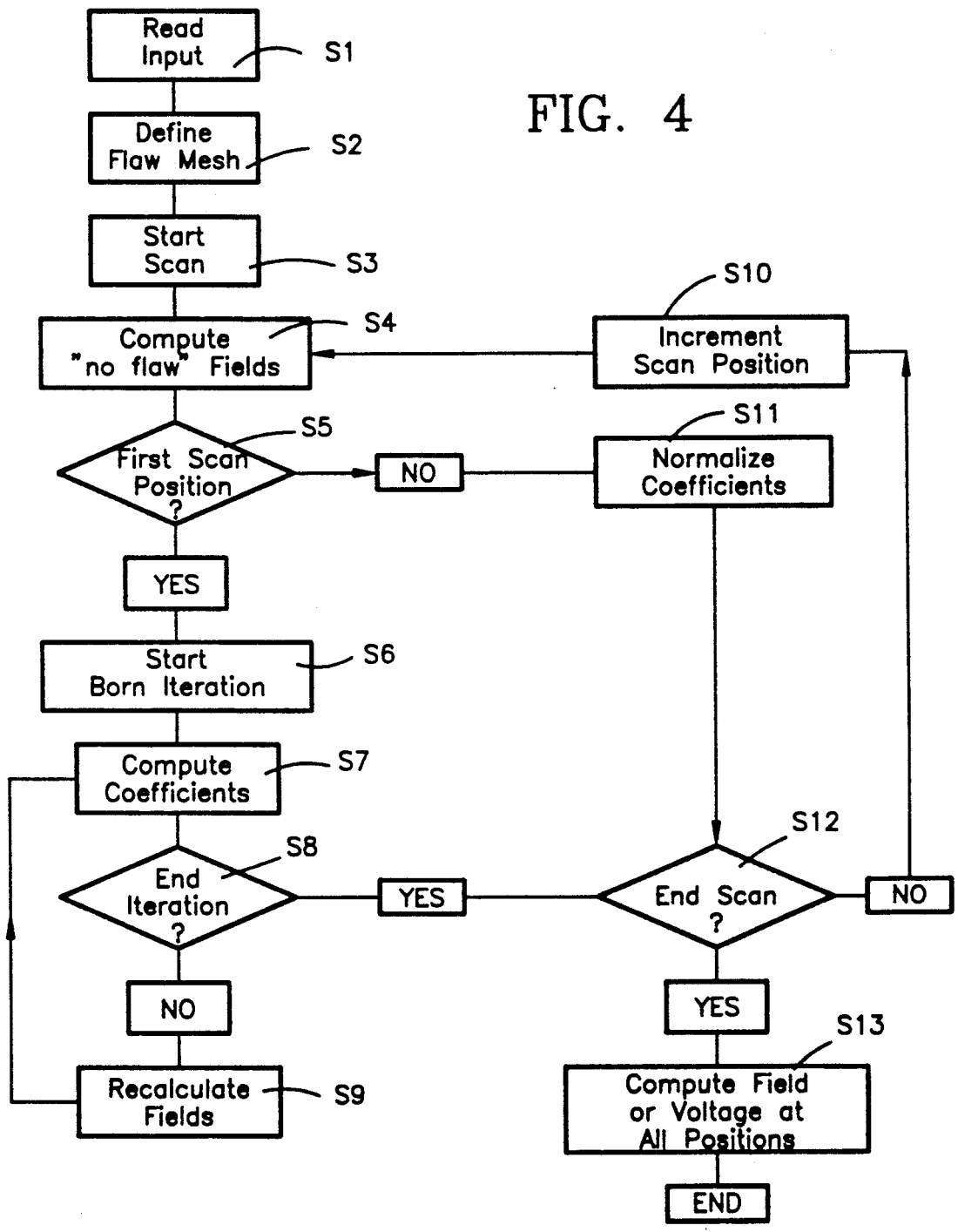
FIG. 4 is a flowchart to help explain the operation of the pipe electromagnetic field simulation apparatus according to the second embodiment of the present invention.

FIG. 4 is a flowchart showing the operation of the second embodiment according to the present invention.

The above-mentioned various data required for simulation is inputted by the input means 1 (step S1), in the various data are included the data indicative of the movement of the transmitting coil and the receiving coil, that is, the data such as the measuring positions from the start point to the end point. Then, the meshing and numbering are performed in only the flaw area (step S2). The entire pipe is not meshed, so that the number of meshes is very few. The number of meshes can be reduced to about several tenths of that where the entire pipe is meshed. Then, simulation is started (step S3).

With the non-flaw analysis means 2, an electromagnetic field distribution is calculated assuming that the pipe has no flaw to determine the magnitude of the electromagnetic field at a place where the flaw exists (step S4).

The theory for the above-mentioned non-flaw analysis is described as follows.

Figure 5:
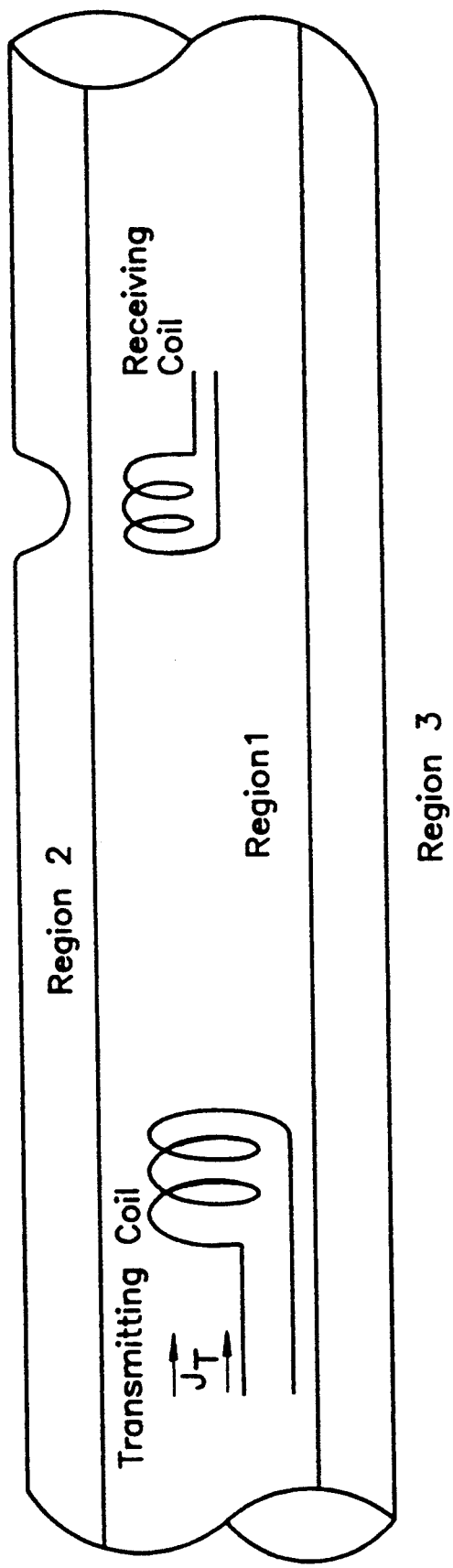
FIG. 5 is a typical view for the electromagnetic field distribution calculation in the present invention.

FIG. 5 shows the transmitting coil, receiving coil, pipe and so on. A voltage produced in the receiving coil is by an electromagnetic induction theory, $$V = i\,\omega \int_{coil} B_1(\text{vector})\cdot n\,(\text{vector})\,dS \cdot \quad (1)$$

Further, because $B_1(\text{vector}) = \nabla \times A_1(\text{vector})$ (here 1 shows a region 1), $A_1(\text{vector})$ is to be obtained. This is apparent from the expression of vector potential of the Maxwell equation.

That is, where a current source $j_s$ (vector) exists in a material (dielectric constant: $\sigma$, permeability; $\mu$), the distribution of the electric field E (vector) and the magnetic field B (vector) in the material will satisfy the following Maxwell equation.

$$\nabla \times E\,(\text{vector}) = -i\,\omega\mu H\,(\text{vector}) \quad (2)$$

$$\nabla \times H\,(\text{vector}) = j\,s\,(\text{vector}) + \sigma E\,(\text{vector}) \quad (3)$$

(reference: NAGAOKA YOUSUKE, "Electromagnetic Science II", Iwanami Shotenn p315)

When the equation (2) is rotated and the equation (3) is substituted, $$\begin{aligned}\nabla \times \nabla \times E\,(\text{vector}) &= -i\,\omega\,\mu\,\nabla \times H\,(\text{vector}) \\ &= -i\,\omega\,\mu\,j\,s\,(\text{vector}) \\ &\quad -i\,\omega\,\mu\,\sigma\,E\,(\text{vector})\end{aligned} \quad (4)$$

Here, a vector potential A {B (vector) = $\nabla \times$ A (vector)}is introduced.

From the equation (2), $$\begin{aligned}\nabla \times E\,(\text{vector} &= -i\,\omega\,B\,(\text{vector}) = -i\,\omega\,\nabla \times A \\ (\text{vector}) &= \nabla \times (-i\,\omega\,A). \\ \therefore E\,(\text{vector}) &= -i\,\omega\,A\,(\text{vector})\end{aligned} \quad (5)$$

When the equation (5) is substituted in the equation (4), $$\nabla \times \nabla \times A\,(\text{vector}) + i\,\omega\mu\sigma A\,(\text{vector}) = \mu j\,s\,(\text{vector}). \quad (6)$$

A vector potential in the pipe when there is the transmitting coil in the pipe and a transmitting current of $J_T(\text{vector})$ flows, is indicated by $A_1(\text{vector})$. Then since $\sigma_1 = 0$, $$\nabla \times = \times A_1\,(\text{vector}) = \mu_0\,j_T\,(\text{vector}). \quad (7)$$
$\mu_0$: permeability of air When a vector potential at a thickness point (part) of the pipe is indicated by $A_2$ (vector).

$$\nabla \times \nabla \times A_2\,(\text{vector}) + i\,\omega\mu\sigma A_2(\text{vector}) = \mu j_F\,(\text{vector}) \quad (8)$$

$j_F(\text{vector})$: current source equivalent to a flaw

When a vector potential outside of the pipe is indicated by $A_3(\text{vector})$.

$$\nabla \times \nabla \times A_3(\text{vector}) = 0 \quad (9)$$

Thus, as mentioned above, it is understood that $A_1$(vector) is obtained from the expression of the vector potential of the Maxwell equation.

Then it is necessary that next three equations are to be resolved for obtaining the $A_1$ (vector).

$$\nabla \times \nabla \times A_1\,(\text{vector}) = \mu_0 j_T(\text{vector}) \quad (10)$$

$$\nabla \times \nabla \times A_2 \text{ (vector)} + i\omega\mu\sigma A_2 \text{(vector)} = \mu j_F \text{ (vector)} \quad (11)$$

$$\nabla \times \nabla \times A_3 \text{(vector)} = 0 \quad (12)$$

Here $j_T$(vector) is a current density of the transmitting coil, $j_F$(vector) is a current density equivalent to the flaw, and $$j_F \text{(vector)} = ((\mu - \mu_\emptyset)/\mu)(\delta(\chi \text{(vector)}) - \chi_s \text{(vector)}(\chi \text{(vector)})))n \text{(vector)} \times H \text{(vector)} - \sigma E \text{(vector)}. \quad (13)$$

$\delta$ is a delta function of Dirac. This is apparent from the calculation method for obtaining a current source equivalent o the flaw.

That is, the Maxwell equation in a material is, $$\nabla \times E \text{ (vector)} = -i\omega\mu(\chi \text{(vector)})H \text{ (vector)} \quad (14)$$

$$\nabla \times H \text{ (vector)} = \sigma(\chi \text{(vector)})E \text{ (vector)}. \quad (15)$$

Next, $B_s$ (vector), $J_s$ (vector) are given by the next equations.

$$B_s \text{(vector)} = [\mu(\chi \text{ (vector)}) - \mu]H \text{ (vector)} \quad (16)$$

$$J_s \text{(vector)} = [\sigma(\chi \text{(vector)}) - \sigma]E \text{ (vector)} \quad (17)$$

$\sigma, \mu$ are constant

The distribution of $\mu(\chi \text{(vector)})$, $\sigma(\chi \text{(vector)})$ are assumed as below.

$$\mu(\chi \text{(vector)}) = \mu_{102} \text{ (within flaw)} \quad (18)$$

$$\mu(\chi \text{(vector)}) = \mu \text{(outside of flaw)} \quad (19)$$

$$\sigma(\chi \text{(vector)}) = 0 \text{ (within flaw)} \quad (20)$$

$$\sigma(\chi \text{(vector)}) = \sigma \text{(outside of flaw)} \quad (21)$$

Therefore, $B_s$ (vector), $J_s$ (vector) are, $$B_s \text{(vector)} = [\mu_{102} - \mu]H \text{ (vector) (within flaw)} \quad (22)$$

$$B_s \text{(vector)} = 0 \text{ (outside of flaw)} \quad (23)$$

$$J_s \text{(vector)} = -\sigma E \text{ (vector) (within flaw)} \quad (24)$$

$$J_s \text{(vector)} = 0 \text{ (outside of flaw)} \quad (25)$$

That is, $B_s$ (vector), $J_s$ (vector) are discontinuous on the surface Of the flaw.

When the equations (16), (17) are substituted to the equations (14), (15), $$\nabla \times E \text{ (vector)} = -1\omega B_s \text{(vector)} - i\omega\mu H \text{ (vector)} \quad (26)$$

$$\nabla \times H \text{ (vector)} = J_s \text{(vector)} + \sigma E \text{ (vector)} \quad (27)$$

When the equation (26) is rotated and the equation (27) is substituted, $$\begin{aligned}\nabla \times \nabla \times E \text{ (vector)} &= -i\omega \nabla \times B_s \text{ (vector)} \\ &\quad -i\omega\mu \nabla \times H \text{ (vector)} \\ &= -i\omega \nabla \times B_s \text{ (vector)} \\ &\quad -i\omega\mu J_s \text{ (vector)} \\ &\quad -i\omega\mu\sigma E \text{ (vector)}\end{aligned}$$

Therefore, $$\nabla \times \nabla \times E \text{ (vector)} + i\omega\mu\sigma E \text{ (vector)} = -i\omega\mu Jf \text{(vector)}. \quad (28)$$

Here, $$Jf \text{(vector)} = (1/\mu)\nabla \times B_s \text{ (vector)} + J_s \text{ (vector)}. \quad (29)$$

When E (vector) = $-i\omega A$ (vector) is substituted in the equation (28) (see the equation (5) in the description about the expression of the vector potential of the Maxwell equation), $$\nabla \times \nabla \times A \text{ (vector)} + i\omega\mu\sigma A \text{ (vector)} = \mu Jf \text{(vector)}. \quad (30)$$

By comparing the equation (29) with the equation (6) in the description about the expression of the vector potential of the Maxwell, it is understood that it is enough to obtain the A (vector) in the uniform material in which a current source Jf (vector) equivalent to the flaw exists, in order to obtain the vector potential A (vector) when the flaw From equations (16) (17, (29), $$\begin{aligned}Jf \text{(vector)} &= (1/\mu)\nabla \times [\mu(\chi \text{ (vector)}) - \mu]H \text{ (vector)} + \\ &\quad [\sigma(\chi \text{ (vector)}) - \sigma]E \text{ (vector)} \\ &= (1/\mu)\nabla[\mu(\chi \text{ (vector)}) - \mu] \times H \text{ (vector)} + \\ &\quad ([\mu(\chi \text{ (vector)}) - \mu]/\mu)\nabla \times H \text{ (vector)} + \\ &\quad (\sigma(\chi \text{ (vector)}) - \sigma]E \text{ (vector)}\end{aligned} \quad (31)$$

Because $\mu(\chi \text{(vector)}) - \mu = 0$ at a place outside of the flaw from the equation (19), and $\mu(\chi \text{(vector)}) - \mu = \mu\emptyset - \mu = \text{const.}$ at a place within the flaw from the equation (18), $\nabla[\mu(\chi \text{(vector)}) = \mu]$ is 0 at a place other than the surface of the flaw.

Here it is assumed that $\mu(\chi \text{(vector)})$ varies from $\mu$ to $\mu_\emptyset$ in a minute interval of the flaw surface.

When a unit vector, which is vertical to the flaw surface and is directed to the flaw from the surface, is indicated by a n (vector).

$$\mu(\chi \text{(vector)}) = \mu - (\xi/\epsilon)(\mu - \mu_\emptyset),$$

$\xi$ is an optional distance in the n (vector) direction. That is, $$\begin{aligned}\nabla[\mu(\chi \text{ (vector)}) - \mu] &= ((\mu - \mu_\emptyset)/\epsilon)\nabla\xi \\ &= -((\mu - \mu_\emptyset)/\epsilon)n \text{ (vector)}\end{aligned}$$

When $\epsilon \to 0$, $$\nabla[\mu(\chi \text{ (vector)}) - \mu] = -(\mu - \mu_\emptyset)\delta(\chi \text{ (vector)} - \chi_s \text{ (vector)}\chi \text{ (vector)}))n \text{ (vector)} \quad (32)$$

$\delta$ is a delta function of Dirac. That is, the equation (32) means that $\nabla[\mu(\chi \text{(vector)}) - \mu]$ is 0 at a place other than the flaw surface.

At the second term of the equation (31), since $\sigma = 0$ within the flaw, $\nabla \times H$ (vector) = 0 from the equation (15).

And outside the flaw, since $\mu(\chi \text{(vector)}) - \mu = 0$, the second term is 0.

At the third term of the equation (31), since $\sigma(\chi\text{(vector)}) - \sigma = 0$ outside the flaw and $\sigma(\chi\text{(vector)}) - \sigma = -\sigma$ within the flaw.

Therefore, the equation (31) is as follows.

$$j_f\text{(vector)} = ((\mu - \mu_\theta)/\mu)\,\delta\,(\chi\text{ (vector)} - \chi_s\text{ (vector)})(\chi\text{ (vector)})\,n\text{ (vector)} \times H\text{ (vector)} - \sigma E\text{ (vector)} \quad (33)$$

Thus the above-mentioned equation (13) is formed.

Therefore, in order to obtain the current $J_f$ (vector) equivalent to the flaw, the H (vector) of the flaw surface and E (vector) within the flaw are necessary.

Then before the equations (10)~(12) are resolved, the next transformation is executed.

$$A_1\text{(vector)} = A_T\text{(vector)} + \nabla A_1\text{ (vector)} \quad (34)$$

Here $A_T$ (vector) is a solution when the transmitting coil exists in a free space, and $\nabla A_1$ (vector) satisfies next homogeneous equation.

$$\nabla \times \nabla \times \Delta A_1 \text{ (vector)} = 0 \quad (35)$$

The $A_1$ (vector) automatically satisfies the boundary condition at an inside surface of the pipe.
Likewise, $$A_2\text{(vector)} = A_\theta\text{(vector)} + A_F\text{ (vector)}. \quad (36)$$

Here, $$\nabla \times \nabla \times A_\theta\text{(vector)} + i\,\omega\mu\sigma A_\theta\text{(vector)} = 0$$

$$\nabla \times \nabla \times A_F\text{(vector)} + i\,\omega\mu\sigma A_F\text{(vector)} = \mu j_F\text{ (vector)}$$

When the equations (10)~(12) are resolved, these equations are transformed to cylindrical coordinates (r, $\phi$, z).

When the vector potential is Fourier-transformed, the following equation is obtained, $$(1/(2\pi))\int_0^{2\pi}\int_{-\infty}^{\infty} A\text{(vector)}(r,\,\phi,\,z)\,e^{-ikz - in\phi}dzd\phi \quad (37)$$

When a method of separating variable is applied to the equations (10)~(12), each coordinate component is as follows.

$$a_z^1 = a_z^T + \alpha_1 J_n(\kappa r)$$
$$a_r^1 = a_r^T + \alpha_2 J_{n+1}(\kappa r) + \alpha_3 J_{n-1}(\kappa r)$$
$$a_\phi^1 = a_\phi^T - i[\alpha_2 J_{n+1}(\kappa r) - \alpha_3 J_{n-1}(\kappa r)]$$
$$a_z^2 = a_z^F + \beta_1 J_n(\lambda r) + \beta_2 H_n^{(1)}(\lambda r)$$
$$a_r^2 = a_r^F + \beta_3 J_{n+1}(\lambda r) + \beta_4 J_{n+1}(\lambda r) +$$
$$\qquad \beta_5 H_{n+1}^{(1)}(\lambda r) + \beta_6 H_{n-1}^{(1)}(\lambda r)$$
$$a_\phi^2 = a_\phi^F - i\,[\beta_3 J_{n+1}(\lambda r) + \beta_4 J_{n+1}(\lambda r) +$$
$$\qquad \beta_5 H_{n+1}^{(1)}(\lambda r) + \beta_6 H_{n-1}^{(1)}(\lambda r)]$$
$$a_z^3 = \gamma_1 K_n + 1(\kappa r)$$
$$a_r^3 = \gamma_2 K_n + 1(\kappa r) + \gamma_3 K_n - 1(\kappa r)$$
$$a_\phi^3 = -i[\gamma_2 K_n + 1(\kappa r) - \gamma_3 K_n - 1(\kappa r)]$$

In the equations, $a^1$ means a component of a region 1, $a^T$ means Fourier-transformation of $A_T$(vector), $a^F$ means Fourier-transformation of $A_F$(vector) of the equation (8).

And $J_n$ means first type Bessel function, $H^{(1)}$ means first type Hankel function, $K = |k|$, $\gamma = I\sqrt{(k^2 + 2i/\delta^2)}$, and $\delta$ means a depth of penetration. And $\alpha$, $\beta$, $\gamma$ are constants which are designated from boundary conditions of inner or outer surface of the pipe.

E (vector), H (vector) at an optional region are given by next equation (39) from a (vector) and permeability $\mu$, $$E(r,\,\phi,\,z) = \frac{i}{2\pi}\sum_n e^{in\phi}\int_{-\infty}^{\infty} a(n,\,r,\,k)e^{ikz}dk$$

$$H_r(r,\,\phi,\,z) =$$

$$\qquad \frac{i}{2\pi\mu r}\sum_n e^{in\phi}\int_{-\infty}^{\infty} [na_z(n,\,rnz) - kra_\phi(n,\,r,\,k)]\,e^{ikz}dk$$

$$H_\phi(r,\,\phi,\,z) =$$

$$\qquad \frac{1}{2\pi\mu}\sum_n e^{in\phi}\int_{-\infty}^{\infty}\left[ika_r(n,\,r,\,k) - \frac{da_z(n,\,r,\,k)}{dr}\right]e^{ikz}dk$$

$$H_z(r,\,\phi,\,z) = \qquad (39)$$

$$\qquad \frac{1}{2\pi\mu r}\sum_n e^{in\phi}\int_{-\infty}^{\infty}\left[\frac{d(ra_\phi(n,\,r,\,k))}{dr} - ina_r(n,\,r,\,k)\right]e^{ikz}dk$$

The boundary conditions for obtaining the constants $\alpha$, $\beta$, $\gamma$ of the equation (38) are, (1) tangent components of E (vector) and H (vector) are continuous at the inner surface and outer surface of the pipe.

(2) At regions of 1, 2, 3, $\nabla \cdot A$ (vector) = 0.

From these conditions, 12 equations for obtaining the 12 unknown numbers of $\alpha$, $\beta$, $\gamma$ are obtained.

As above-described by using the equations (1)–(39), the premise theory for analyzing the electromagnetic distribution is obtained.

Now assuming that no flaw exists, $a^F$(vector) = 0 and of the components of a(vector), those other than a $\phi$ become zero. This allows the matter of the boundary values with respect to electromagnetic field distribution to be very simply calculated and the constant $\beta$ to be easily determined.

Then, whether the position of the transmitting coil and the receiving coil is located on their start point or not is checked (step S5).

When the position is located on the start point, the second equivalent current calculation means 6 determines a current source equivalent to the flaw by utilizing the various data inputted from the input means 1 and the results analyzed by said non-flaw analysis means 2, and by performing repeatedly a calculation according to the Born's approximation rule (steps S6 through S9).

That is, in order to solve the above-mentioned equations (Nos. 10 through 12), $j_F$ (vector) becomes necessary, whereby it is necessary to know the E (vector) and the H (vector) in the flaw. However, in order to determine the E (vector) and the H (vector) in an arbitrary position, it is necessary to know $a_F$ (vector), that is, $j_F$ (vector) as apparent from the equations (Nos. 38 and 39). Thus, the Born's approximation rule is utilized to determine the E (vector) and the H (vector) in the flaw.

First, the E (vector) and the H (vector) where no flaw exists are determined in such a manner as described above. These E (vector) and H (vector) as primary approximations are substituted in the equation (No. 13) to determine $j_F$ (vector). With this $j_F$ (vector) and the equations (Nos. 38 and 39), new E (vector) and H (vector) where the flaws exists are to be determined. Then, these new E (vector) and H (vector) as secondary approximation are substituted in the equation (No. 13) to determine new $j_F$ (vector). With this new $j_F$ (vector), more accurate E (vector) and H (vector) where the flaw exists are to be determined (step S7). This repeated calculation is performed repeatedly until the E (vector) and the H (vector) converge, that is, the deviation of the results calculated becomes 5% or less (steps S8, S9, S7). Usually, with the calculation repeated four times, the E (vector) and the H (vector) may converge.

When the E (vector) and the H (vector) converge, a final a (vector), that is, a vector potential A (vector) is determined (step S8).

Then, whether the position of the transmitting coil reaches the end point or not is judged (step S12). When the position of the transmitting coil does not reach the end point, the position is allowed to advance by one step (step S10). Then, the operation is returned to the above-mentioned step S4. In this case, in the second embodiment, the method of determining the equivalent current source has been made simple. That is, the equivalent current source is determined by making the equivalent current source proportional to the magnitude of the electromagnetic field, in the flaw position for non-flaw, obtained by the non-flaw analysis means 2 and thus correcting the equivalent current source value previously determined (step S11).

When the transmitting coil does not still come to the end point (step S12), the equivalent current source value corresponding to the position of the transmitting coil is determined by allowing the transmitting coil to advance further by one step, and by correcting the equivalent current source value previously determined. Such simple method allows the calculation time to be reduced to several hundredths.

Without using such simple method, for the second and the following positions of the transmitting coil, the Born's approximation rule may be utilized in a similar manner to that used for the start point. This embodiment is also included in the claims.

Thus, when the transmitting coil comes to the final point (step S12), the pipe electromagnetic field distribution is obtained by the use of the vector potential having been determined (step S13).

Finally, the display means 5 displays the pipe electromagnetic field distribution.

FIG. 6 is a block diagram showing a third embodiment of the present invention.

The third embodiment is different from the first embodiment in that the third embodiment has flaw detecting signal calculation means 7 for calculating a flaw detecting signal occurring in the receiving coil taking into account the results obtained by the pipe electromagnetic field analysis means 4.

That is, a signal occurring in the receiving coil is determined from the electromagnetic field distribution obtained by the pipe electromagnetic field analysis means 4.

Specifically, based on the vector potential A (vector determined as described above, a voltage V occurring in the receiving coil is obtained from the equation (No. 1).

FIG. 7 is a block diagram showing a fourth embodiment of the present invention. The fourth embodiment is different from the second embodiment in that the fourth embodiment has flaw detecting signal calculation means 7 for calculating a flaw detecting signal occurring in the receiving coil taking into account the results obtained by the pipe electromagnetic field analysis means 4. Its contents, having been described above, will be omitted.

Having been embodied in software above-mentioned embodiments by the use of a computer in the means of the present invention, a special hardware circuit may be used without being limited to the computer.

According to the present invention as described above, a simulation technique is used, whereby it is unnecessary to produce several kinds of transmitting coils and receiving coils practically corresponding to the pipe to be detected for flaw, and it is possible to make the calculation time short and to make the required computer capacity small.

What is claimed is:

1. A pipe electromagnetic field simulation apparatus, comprising:

input means for providing input data, said input data including first input data representative of physical characteristics of a pipe to be detected for a flaw, second input data representative of physical characteristics of a transmitting coil, third input data representative of an exciting frequency applied to said represented transmitting coil for examining said represented pipe, and fourth data representative of physical characteristics of a flaw in said represented pipe;

non-flaw analysis means for determining, based on said first, second and third input data, first determined data representative of an electromagnetic field distribution of said represented pipe when no flaw is present in said represented pipe;

equivalent current source determining means for determining second determined data representative of a current source equivalent to a current source which would be produced in said pipe by said represented flaw occurring in said represented pipe when said represented pipe is examined under said represented exciting frequency, said first equivalent current source determining means determining said second determined data from a repeated calculation according to Born's approximation rule to calculate a vector of a distribution of a magnetic field and a vector of a distribution of an electric field at a position of said represented flaw in said represented pipe using said first determined data from said non-flaw analysis means, said first input data, said second input data, said third input data and said fourth input data; and pipe electromagnetic field analysis means for determining third determined data representative of an electromagnetic field distribution of said represented pipe using said second determined data.

2. A pipe electromagnetic field simulation apparatus, comprising:

input means for providing input data, said input data including first input data representative of physical characteristics of a pipe to be detected for a flaw, second input data representative of physical characteristics of a transmitting coil, third input data representative of an exciting frequency applied to said represented transmitting coil for examining said represented pipe, and fourth data representative of physical characteristics of a flaw in said represented pipe;

non-flaw analysis means for determining, based on said first, second and third input data, first determined data representative of an electromagnetic field distribution of said represented pipe when no flaw is present in said represented pipe;

equivalent current source determining means for determining second determined data representative of a current source equivalent to a current source which would be produced in said pipe by said represented flaw occurring in said represented pipe when said represented pipe is examined under said represented exciting frequency, said first equivalent current source determining means determining said second determined data for (1) a first position of said represented transmitting coil relative to said represented pipe from a repeated calculation according to Born's approximation rule to calculate a vector of a distribution of a magnetic field and a vector of a distribution of an electric field at a position of said represented flaw in said represented pipe using said first determined data from said non-flaw analysis means, said first input data, said second input data, said third input data and said fourth input data, and (2) a second and subsequent positions of said represented transmitting coil relative to said pipe by determining said second determined data to be proportional to said first determined data for said second and subsequent positions; and pipe electromagnetic field analysis means for determining third determined data representative of an electromagnetic field distribution of said represented pipe using said second determined data.

3. A pipe electromagnetic field simulation apparatus, comprising:

input means for providing input data, said input data including first input data representative of physical characteristics of a pipe to be detected for a flaw, second input data representative of physical characteristics of a transmitting coil, third input data representative of an exciting frequency applied to said represented transmitting coil for examining said represented pipe, fourth data representative of physical characteristics of a flaw in said represented pipe, fifth input data representative of physical characteristics of a receiving coil, and sixth input data representative of a distance between said represented transmitting and receiving coils;

non-flaw analysis means for determining, based on said first, second and third input data, first determined data representative of an electromagnetic field distribution of said represented pipe when no flaw is present in said represented pipe;

equivalent current source determining means for determining second determined data representative of a current source equivalent to a current source which would be produced in said pipe by said represented flaw occurring in said represented pipe when said represented pipe is examined under said represented exciting frequency, said first equivalent current source determining means determining said second determined data from a repeated calculation according to Born's approximation rule to calculate a vector of a distribution of a magnetic field and a vector of a distribution of an electric field at a position of said represented flaw in said represented pipe using said first determined data from said non-flaw analysis means, said first input data, said second input data, said third input data and said fourth input data;

pipe electromagnetic field analysis means for determining third determined data representative of an electromagnetic field distribution of said represented pipe using said second determined data; and flaw signal detecting means for determining a flaw signal produced in said represented receiving coil by said represented flaw based upon said third determined data provided by said pipe electromagnetic field analysis means, said fifth input data, and said sixth input data.

4. A pipe electromagnetic field simulation apparatus, comprising:

input means for providing input data, said input data including first input data representative of physical characteristics of a pipe to be detected for a flaw, second input data representative of physical characteristics of a transmitting coil, third input data representative of an exciting frequency applied to said represented transmitting coil for examining said represented pipe, fourth data representative of physical characteristics of a flaw in said represented pipe, fifth data representative of physical characteristics of a receiving coil, and sixth input data representative of a distance between said represented transmitting and receiving coils;

non-flaw analysis means for determining, based on said first, second and third input data, first determined data representative of an electromagnetic field distribution of said represented pipe when no flaw is present in said represented pipe;

equivalent current source determining means for determining second determined data representative of a current source equivalent to a current source which would be produced in said pipe by said represented flaw occurring in said represented pipe when said represented pipe is examined under said represented exciting frequency, said first equivalent current source determining means determining said second determined data for (1) a first position of said represented transmitting coil relative to said represented pipe from a repeated calculation according to Born's approximation rule to calculate a vector of a distribution of a magnetic field and a vector of a distribution of an electric field at a position of said represented flaw in said represented pipe using said first determined data from said non-flaw analysis means, said first input data, said second input data, said third input data and said fourth input data, and (2) a second and subsequent positions of said represented transmitting coil relative to said pipe by determining said second determined data to be proportional to said first determined data for said second and subsequent positions;

pipe electromagnetic field analysis means for determining third determined data representative of an electromagnetic field distribution of said represented pipe using said second determined data; and flaw signal detecting means for determining a represented flaw signal produced in said represented receiving coil by said represented flaw based upon said third determined data provided by said pipe electromagnetic field analysis means, said fifth input data and said sixth input data.

* * * * *